United States Patent [19]
Katoh et al.

[11] Patent Number: 5,283,357
[45] Date of Patent: Feb. 1, 1994

[54] SEPARATION METHOD OF ALPHA-L-ASPARTYL-L-PHENYLALANINE METHYL ESTER

[75] Inventors: Toshio Katoh, Kawasaki; Chojiro Higuchi, Kamakura; Takeshi Oura, Zushi; Masanobu Ajioka, Yokohama; Akihiro Yamaguchi, Kamakura, all of Japan

[73] Assignee: Mitsui Toatsu Chemicals, Incorporated, Tokyo, Japan

[21] Appl. No.: 688,709

[22] Filed: Apr. 23, 1991

Related U.S. Application Data

[63] Continuation of Ser. No. 322,384, Mar. 13, 1989, abandoned.

[30] Foreign Application Priority Data

| Mar. 14, 1988 | [JP] | Japan | 63-058210 |
| Jun. 1, 1988 | [JP] | Japan | 63-135060 |
| Jun. 13, 1988 | [JP] | Japan | 63-143673 |
| Jun. 27, 1988 | [JP] | Japan | 63-156866 |

[51] Int. Cl.⁵ .................. C07C 227/34; C07C 227/38
[52] U.S. Cl. ........................................ 560/41; 562/450
[58] Field of Search ......................... 560/41; 562/450

[56] References Cited

U.S. PATENT DOCUMENTS

| 3,786,039 | 1/1974 | Ariyoshi et al. | 260/112.5 |
| 3,798,207 | 3/1974 | Ariyoshi et al. | 260/112.5 |
| 3,933,781 | 1/1976 | Bachman et al. | 260/112.5 |
| 3,962,207 | 6/1976 | Uchimaya et al. | 560/41 |
| 4,173,562 | 11/1979 | Bachman et al. | 260/112.5 R |
| 4,375,430 | 3/1983 | Sklavounos | 549/88 |
| 4,465,626 | 8/1984 | Sklavounos | 549/88 |
| 4,549,987 | 10/1985 | Dallatomasina et al. | 562/450 |
| 4,656,304 | 4/1987 | Oppici et al. | 560/41 |
| 4,803,300 | 2/1989 | Hijiya et al. | 562/450 |

FOREIGN PATENT DOCUMENTS

| 0095772A1 | 12/1983 | European Pat. Off. |
| 2550538 | 2/1985 | France |
| 49-6305 | 2/1974 | Japan |
| 57-25537 | 5/1982 | Japan |
| 57-25538 | 5/1982 | Japan |
| 60-67497 | 4/1985 | Japan |
| 2140805A | 12/1984 | United Kingdom |
| 2140805 | 12/1984 | United Kingdom |

*Primary Examiner*—Paul J. Killos
*Assistant Examiner*—B. Frazier
*Attorney, Agent, or Firm*—Millen, White, Zelano & Branigan

[57] ABSTRACT

A method for separating α-L-aspartyl-L-phenylalanine methyl ester (α-APM) from a solution containing α-APM and impurities associated with the production thereof which comprises adding a mineral acid or an organic sulfonic acid to the solution in an organic carboxylic acid or in a solvent containing an organic carboxylic acid, and isolating the pure salt of α-APM which precipitates therefrom.

24 Claims, No Drawings

SEPARATION METHOD OF ALPHA-L-ASPARTYL-L-PHENYLALANINE METHYL ESTER

This application is a continuation of application Ser. No. 07/322,384, filed Mar. 13, 1989, now abandoned.

BACKGROUND OF THE INVENTION

1. Field of the Invention

The present invention relates to a method for separating α-L-aspartyl-L-phenylalanine methyl ester (α-APM) from a solution containing α-APM and impurities associated with the production thereof.

2. Description of the Prior Art

α-L-aspartyl-L-phenylalanine methyl ester (hereinafter abbreviated as α-APM) has been widely known as a dipeptide base sweetener. It has sweetness of good quality and a sweetness degree of about 200 times the sweetness of sucrose. The demand for α-APM is now rapidly expanding as a diet sweetener.

α-APM is a dipeptide compound composed of L-aspartic acid and L-phenylalanine methyl ester. Various methods have already been disclosed for the preparation of α-APM. These methods are primarily chemical processes and generally employ L-aspartic acid anhydride having a protected amino group as a starting material.

For example, it has been known that L-aspartic acid anhydride having a protected amino group can be subjected to a condensation reaction with L-phenylalanine methyl ester in a suitable solvent, and the protective group can be subsequently cleaved with a usual method to obtain α-APM (U.S. Pat. No. 3,786,039). A process for the preparation of α-APM from materials other than L-phenylalanine methyl ester is disclosed in U.S. Pat. No. 3,933,781. In the process, N-formyl-L-aspartic acid anhydride is subjected to a condensation reaction with L-phenylalanine in acetic acid and subsequently deformylated in the presence of hydrogen halide. The resultant intermediate is esterified by treating with water, alcohol and hydrogen halide. Then α-APM is isolated in the form of a hydrogen halide salt.

U.S. Pat. No. 4,173,562 describes another process in which N-formyl-L-aspartic acid anhydride is subjected to a condensation reaction with L-phenylalanine, and then deformylation and esterification are simultaneously carried out to produce α-APM.

U.S Pat. No. 3,962,207 also teaches a process using a mineral acid salt of L-aspartic acid anhydride. The mineral acid salt is reacted with L-phenylalanine methyl ester in a solvent mixture consisting of strong acid, water and methanol. α-APM is isolated from the solvent mixture in the form of a strong acid salt of α-APM.

In each of the above processes, however, β-L-aspartyl-L-phenylalanine methyl ester (hereinafter abbreviated as β-APM) is inevitably formed as a by-product in addition to the desired α-APM. β-APM has no sweet flavor and instead exhibits a bitter taste. Therefore, contamination therewith decreases the commodity value of α-APM.

When an N-acyl group, for example, an N-formyl group, is used as a protective group, the protective group is generally removed by bringing the group into contact with a strong acid.

Under these conditions, however, the methyl ester group of α-APM is liable to undergo partial hydrolysis. In the presence of methanol, α-L-aspartyl-L-phenylalanine-β-methyl ester and/or α-L-aspartyl-L-phenylalanine dimethyl ester are formed as by-products, and thus it is difficult to selectively obtain only the desired α-APM.

On the other hand, when a benzyloxycarbonyl group is used as the protective group, the protective group can be readily removed by catalytic reduction, thereby eliminating the problem of hydrolyzing methyl ester. Thus it is known that this protective group is capable of being removed with high selectivity. Japanese Patent Publication Nos. 25537/1982 and 25538/1982 disclose a process wherein benzyloxycarbonylaspartic acid anhydride is reacted with L-phenylalanine methyl ester, the resultant N-benzyloxycarbonyl-L-aspartyl-L-phenylalanine methyl ester (hereinafter abbreviated as Z-APM) is hydrogenated in the presence of an aqueous mineral acid solution, and the reaction mixture thus obtained is neutralized to give α-APM. The process, however, also forms β-APM as a by-product and an aqueous mineral acid solution is employed in order to remove the protective group. Therefore, the methyl ester group of α-APM is apt to hydrolyze while removing the N-benzyloxycarbonyl group. A catalytic reduction process in an acetic acid is also described in the patent publication. Diketopiperazine derivatives are formed in the step of distilling off acetic acid after completing the catalytic reduction, which decreases the yield of α-APM. The diketopiperazine derivatives also have no sweet flavor and their contamination adversely affects the commodity value of α-APM.

In addition, it is known as a conventional separation method to bring a mixture of α- and β-APM into contact with β-resorcylic acid in an aqueous medium. In the method, α-APM forms a slightly soluble adduct and separates from the contaminating β-APM (Japanese Patent Publication No. 6305/1974).

Although the method can separate α-APM from its impurities contained in a large amount, β-resorcylic acid is required in the same amount as that of the α- and β-APM. In the method, the β-resorcylic acid adduct of α-APM is isolated from a dilute aqueous solution, the β-resorcylic acid is recovered using organic solvents and the like, and the resultant aqueous solution is further concentrated under reduced pressure. Then the isolated α-APM is recrystallized from water. Separation procedures are, therefore, complex; and the recovery rate of the expensive α-APM is low, thereby making the method economically unfavorable.

U.S. Pat. No. 3,798,207 discloses a method wherein an only slightly soluble hydrogen halide salt of 60 -APM is formed by bringing α-APM into contact with hydrogen halide in an aqueous medium in order to separate therefrom β-APM coexisting as an impurity. The method leads to good separation of α- and β-APM. However, hydrolysis of the methyl ester group of the α-APM tends to proceed concurrently because a dilute aqueous solution of hydrogen halide is used. Use of the hydrogen halide solution in an excess amount enables good separation of α-APM from the impurities. On the other hand, a disadvantage the method is that the recovery rate of the hydrogen halide salt of α-APM is low.

As mentioned above, any separation methods of α-APM which have been known to date are disadvantageous and unsatisfactory in view of the industrial separation and purification methods involved.

SUMMARY OF THE INVENTION

The object of this invention is to provide a method which lacks the industrial disadvantages such as those mentioned-above for the conventional separation methods and which is capable of efficiently separating high-purity α-APM from a solution containing α-APM and impurities associated with the production thereof.

The method of this invention involves separation of α-APM from a solution thereof in an organic carboxylic acid, as its mineral acid or organic sulfonic acid salt.

In one aspect, the method of this invention comprises the steps of:

(1) dissolving or suspending crude α-APM in an organic carboxylic acid or an organic solvent containing the organic carboxylic acid;

(2) adding a mineral acid or an organic sulfonic acid to the resultant mixture, i.e., solution or suspension in order to form a mineral acid salt or an organic sulfonic acid salt of α-APM; and (3) separating the thus-produced insoluble mineral acid salt or organic sulfonic acid salt of α-APM.

According to the method of this invention, crude αAPM is brought into contact with a mineral acid or an organic sulfonic acid while in admixture with an organic carboxylic acid or in an organic solvent containing the organic carboxylic acid. The only slightly soluble mineral acid salt or organic sulfonic acid salt of α-APM precipitates from solution or remains undissolved therein. On the other hand, the impurities conventionally present in crude α-APM, such as β-APM, α-L-aspartyl-L-phenylalanine and diketopiperazine derivatives, remain in the solution or are dissolved therein. The thus purified α-APM in the form of a salt of the mineral acid or the organic sulfonic acid, can be recovered in a high yield.

The crude α-APM used as starting material in the method of this invention may be obtained by any process. L-phenylalanine methyl ester or L-phenylalanine is used as a starting material and is subjected to a condensation reaction with N-protected L-aspartic acid anhydride. Then a reaction for removing the protecting group or a reaction for protecting group removal and esterification is carried out to give crude α-APM. Purified α-APM can be separated from the thus-produced crude α-APM by the method of this invention.

In particular, benzyloxycarbonyl group is used for the protection of aspartic acid anhydride. The resultant benzyloxycarbonylaspartic acid anhydride is reacted with L-phenylalanine methyl ester. The crude Z-APM thus obtained is hydrogenated in the organic carboxylic acid or in the organic solvent containing the organic carboxylic acid. The resulting reaction mixture can be treated by the method of this invention to separate purified α-APM without isolating crude α-APM.

Crude α-APM prepared by the above processes generally contains one or more contaminants, such as β-APM and its hydrolyzed products, hydrolyzed products of α-APM, diester compounds, and diketopiperazine derivatives. Crude α-APM consisting essentially of α-APM and β-APM is preferred. Crude α-APM having α-APM contents ranging from 50% to 95% can be advantageously purified by the method of this invention. Industrially, the starting crude products usually have α-APM contents in the range of 70% to 90%.

The organic carboxylic acids which can be used as solvent in the method of this invention includes, for example, aliphatic carboxylic acids such as lower-fatty acids, e.g., acetic acid and propionic acid. Acetic acid is preferably used. A solid aliphatic carboxylic acid is also used, if dissolved in another solvent.

A mixture of the organic carboxylic acid and a volatile organic solvent miscible therewith can be favorably employed so long as the solvent does not inhibit formation of the mineral acid salt or the organic sulfonic acid salt of α-APM. Representative examples of solvents which can be used for the solvent mixture containing the organic carboxylic acid include hydrocarbons such as toluene, xylene and hexane; carboxylic acid esters such as ethyl acetate and butyl acetate; and ethers such as tetrahydrofuran and dioxane.

There is no particular restriction as to the amount of the organic carboxylic acid and organic solvent used, provided an amount sufficient to dissolve the salts of the impurities in the α-APM is employed. The preferred amount is in the range of 3–10 times the weight of starting crude α-APM.

The mineral acids which can be used in the method of this invention include, for example, sulfuric acid, nitric acid, phosphoric acid, hydrochloric acid and hydrogen chloride gas, the preferred mineral acid being sulfuric acid. No particular restriction is placed on the concentration of the mineral acid employed. However, mineral acids with a high water content tend to cause hydrolysis of the α-APM ester group and simultaneously increases the solubility of α-APM salts, which causes lowering in the yield of α-APM. Therefore, more concentrated acids are preferred, e.g., 95–98% sulfuric and 30–37% hydrochloric acids.

The quantity of the mineral acid which is employed is at least the theoretical amount required to form the corresponding salts α- and β-APM or other base in the solution. Use of the acid in slight chemical equivalent excess is usually sufficient. No particular restriction is imposed on the temperature at which the mineral acid is added. However, an excessively high temperature promotes hydrolysis of α-APM and tends to lower the yield of the α-APM salt thus produced. The preferred temperature is usually in the range of 10°–50° C.

The organic sulfonic acids which can be used in the method of this invention include, for example, aliphatic and aromatic sulfonic acids such as methane-sulfonic acid, ethanesulfonic acid, benzenesulfonic acid, p-toluenesulfonic acid, trifluoromethanesulfonic acid and naphthalenesulfonic acid. Methanesulfonic acid is preferred among these sulfonic acids.

The quantity of the organic sulfonic acid which is employed is the theoretical amount required to convert the α-APM, β-APM and any other bases in the solution into sulfonic acid salts. Use of a slight excess chemical equivalent of the sulfonic acid is usually sufficient. The preferred temperature of adding the organic sulfonic acid is usually 10°–50° C.

In conducting one aspect of the method of this invention, the starting crude α-APM is dissolved or suspended in an organic carboxylic acid or in an organic solvent containing an organic carboxylic acid. When the mineral acid or the organic sulfonic acid is added to the resultant solution or suspension, the insoluble mineral acid or the organic sulfonic acid salt of α-APM is produced, usually as crystals. The insoluble solids are isolated in a conventional manner, filtered and washed, to isolate the pure mineral acid salt or the organic sulfonic acid salt of α-APM.

In another aspect of the method of this invention, crude Z-APM is dissolved or suspended in the organic carboxylic acid or in the solvent containing the organic carboxylic acid and stirred in a hydrogen atmosphere in the presence of a reducing catalyst. After completing the reduction (and removing the reduction catalyst, if insoluble), the mineral acid or organic sulfonic acid is added to the reaction mixture. The resultant α-APM mineral acid or the organic sulfonic acid salt of α-APM precipitates from solution and can be merely filtered and washed to isolate the pure mineral acid salt or the organic sulfonic acid salt of α-APM.

As to the reducing catalyst used in the hydrogenation reaction, iron group metals or platinum group metals can be used. The catalyst may be used in the form of intact metals or those supported on a carrier. Preferred catalysts are noble metal base catalysts supported on a carbon carrier such as platinum carbon, palladium carbon and the like. There is no particular restriction on the amount of the catalyst used. The preferred amount ranges 0.01-1% by weight of crude Z-APM as converted to the weight of catalyst metals. A hydrogenation temperature in the range of $-10°$ to $80°$ C. is preferred for stabilizing crude Z-α-APM and the product α-APM. The hydrogenation may also be carried out under elevated pressure, but the reaction proceeds sufficiently at atmospheric pressure. The hydrogenation time varies depending upon the solvent, catalyst and temperature. When suitable conditions are selected, the hydrogenation can be completed in 1-5 hours.

Free α-APM can be obtained conventionally from the mineral acid salt or the organic sulfonic acid salt of α-APM which is isolated by the method of this invention. For example, the mineral acid salt or the organic sulfonic acid salt of α-APM can be dissolved in water and the pH of the resulting solution adjusted to the isoelectric point of α-APM by the addition of an inorganic base such as sodium hydrogen carbonate, potassium hydrogen carbonate, sodium carbonate, potassium carbonate and ammonia or an organic base such as triethylamine and picoline. These inorganic and organic bases are usually used for neutralization. Thus α-APM can be In accordance with the method of this invention, the mineral acid salt or the organic sulfonic acid salt of α-APM alone can be readily separated by simple procedures from crude α-APM containing β-APM and/or other impurities.

The protecting group of crude Z-APM can be removed in a high yield. Thereafter, the mineral acid or the organic sulfonic acid is merely added to the reaction mixture to separate the mineral acid salt or the organic acid salt of α-APM unpurified form therefrom. It is unnecessary to first separate α-APM from the reaction mixture containing the β-APM and/or other impurities. In addition, the isolation in accordance with the method of this invention can be conducted in a high yield as compared with the conventional methods.

Therefore, the method of this invention is industrially very valuable for the separation of α-APM.

EXAMPLES

The method of this invention will hereinafter be illustrated in detail by way of the following examples.

EXAMPLE 1

To 133.2 g of an acetic acid solution containing 22.1 g (0.075 mole) of α-APM and 7.4 g (0.025 mole) of β-APM, 10.5 g (0.105 mole) of 98% sulfuric acid was added over 30 minutes at $20°-25°$ C. The mixture was stirred for an hour at the same temperature. Thereafter the precipitated crystals were filtered, washed and dried. The isolated crystals of sulfuric acid salt weighed 29.6 g. The crystals thus obtained was analyzed by high performance liquid chromatography. The α-APM content converted to free amine was 20.8 g, which corresponded to a recovery ratio of 94% of the original α-APM. The ratio of α-APM:β-APM was 99.0:1.0. Elementary analysis data were consistent with the sulfuric acid salt of α-APM.

| Elementary analysis (%) $C_{14}H_{20}N_2O_9S$ | | | | |
|---|---|---|---|---|
| | C | H | N | S |
| Found | 42.72 | 5.34 | 7.14 | 8.16 |
| Calculated | 42.86 | 5.14 | 7.14 | 8.17 |

EXAMPLE 2

To 133.2 g of an acetic acid solution containing 23.5 g (0.08 mole) of α-APM and 5.9 g (0.02 mole) of β-APM, 10.5 g (0.105 mole) of 98% sulfuric acid was added over 30 minutes at $20°-25°$ C. The mixture was stirred for an hour at the same temperature. Thereafter the precipitated crystals were filtered, washed and dried. The isolated crystals of sulfuric acid salt weighed 30.9 g. The crystals thus obtained were analyzed by high performance liquid chromatography. The α-APM content converted to free amine was 22.9 g, which corresponded to a recovery of 97.5% of the original α-APM. The ratio of α-APM:βAPM was 99.0:1.0.

To 178 g of water, 20 g of the crystals was added. The solution thus obtained was adjusted to pH 5.2 by the addition of sodium hydrogen carbonate and cooled to $5°$ C. Precipitated crystals were filtered, washed with cold water and dried. The yield of crystalline α-APM was 18.8 g.

Angle of rotation: $[\alpha]_D^{20} + 15.8$ ($C = 4.15 N$ formic acid)

According to analysis by high performance liquid chromatography, the crystals thus obtained were high purity α-APM.

EXAMPLE 3

To 133.2 g of an acetic acid solution containing 30.0 g (0.10 mole as a sum of α-APM and β-APM crude α-APM which contains 95.6% of α-APM and 4.1% of β-APM as a contaminant, 10.5 g (0.105 mole) of 98% sulfuric acid was added over 30 minutes at $20°-25°$ C. The mixture was stirred for an hour at the same temperature. Thereafter the precipitated crystals were filtered, washed and dried. The isolated crystals of the sulfuric acid salt of α-APM were 38.6 g.

The crystals thus obtained were analyzed by high performance liquid chromatography. The purity was 99.1% as sulfuric acid salt of α-APM and the content of sulfuric acid salt of β-APM was 0.5%. The yield was 97.4%.

The results of elementary analysis coincided with the sulfuric acid salt of α-APM.

| Elementary analysis (%) $C_{14}H_{20}N_2O_9S$ | | | | |
|---|---|---|---|---|
| | C | H | N | S |
| Found | 42.76 | 5.33 | 7.12 | 8.16 |

-continued

| Elementary analysis (%) $C_{14}H_{20}N_2O_9S$ | | | |
|---|---|---|---|
| C | H | N | S |
| Calculated 42.86 | 5.14 | 7.14 | 8.17 |

To 178 g of water, 20 g of the thus-obtained crystals were added. The solution thus obtained was adjusted to pH 5.2 by the addition of sodium hydrogen carbonate and cooled to 5° C. The crystals which precipitated were filtered, washed with cold water and dried. The yield of crystalline α-APM was 18.8 g.

Angle of rotation: $[\alpha]_D^{20} + 15.8$ ($C=4.15N$ formic acid)

According to the analysis by high performance liquid chromatography, the crystals thus obtained were high purity α-APM.

EXAMPLE 4

To 294 g of an acetic acid solution containing 30.0 g (0.10 mole as a sum of α-APM and β-APM) of crude α-APM having the same composition as described in Example 3, 11.0 g (0.105 mole) of 35% hydrochloric acid was added over 30 minutes at 20°–25° C. The mixture was stirred for an hour at the same temperature. Thereafter the precipitated crystals were filtered, washed and dried. The isolated, crystals of the hydrochloric acid salt of α-APM weighed 32.1 g.

The crystals thus obtained were analyzed by high performance liquid chromatography. The purity was 99.6% as the hydrochloric acid salt of α-APM and the content of hydrochloric acid salt of β-APM was 0.3%.
The yield was 94.9%.
Results of elementary analysis coincided with the hydrochloric acid salt of α-APM.

| Elementary analysis (%) $C_{14}H_{19}Cl\ N_2O_5$ | | | |
|---|---|---|---|
| C | H | N | Cl |
| Found 50.70 | 5.83 | 8.35 | 10.53 |
| Calculated 50.84 | 5.79 | 8.47 | 10.72 |

EXAMPLE 5

To 133.2 g of an acetic acid solution containing 23.5 g (0.08 mole) of αAPM, 5.9 g (0.02 mole) of β-APM and 2.5 g (0.0089 mole) of α-L-aspartyl-L-phenylalanine, 11.4 g (0.114 mole) of 98% sulfuric acid was added over 30 minutes at 20°–25° C. The mixture was stirred for an hour at the same temperature. Thereafter the precipitated crystals were filtered, washed and dried. The isolated crystals of sulfuric acid salt weighed 30.6 g. The crystals thus obtained were analyzed by high performance liquid chromatography. The α-APM content converted to free amine was 22.8 g.

Results of elementary analysis coincided with the sulfuric acid salt of α-APM.

The recovery based on to original α-APM was 97.0%.

EXAMPLE 6

To 235 g of an acetic acid solution containing 23.5 g (0.08 mole) of α-APM, 5.9 g (0.02 mole) of β-APM, 2.5 g (0.0089 mole) of α-L-aspartyl-L-phenylalanine and 0.6 g (0.0021 mole) of β-L-aspartyl-L-phenylalanine, 11.7 g (0.117 mole) of 98% sulfuric acid was added over 30 minutes at 20°–25° C. The mixture was stirred for an hour at the same temperature. Thereafter the precipitated crystals were filtered, washed and dried. The isolated crystals of the sulfuric acid salt of α-APM weighed 29.4 g. The crystals thus obtained were analyzed by high performance liquid chromatography. The α-APM content converted to free amine was 21.9 g. The ratio of α-APM:βAPM was 99.5:0.5.

The recovery based on to original α-APM was 93.2%.

EXAMPLE 7

To 235 g of an acetic acid solution containing 23.5 g (0.08 mole) of α-APM, 5.9 g (0.02 mole) of β-APM, 2.5 g (0.0089 mole) of α-L-aspartyl-L-phenylalanine, 0.6 g (0.0021 mole) of δ-L-aspartyl-L-phenylalanine and 0.6 g (0.0023 mole) of 5-benzyl-3,6-dioxopiperazine-2-acetic acid, 11.7 g (0.117 mole) of 98% sulfuric acid was added over 30 minutes at 20°–25° C. The mixture was stirred for an hour at the same temperature. Thereafter the precipitated crystals were filtered, washed and dried. The isolated crystals of the sulfuric acid salt of α-APM were 29.0 g. The crystals thus obtained weighed analyzed by high performance liquid chromatography. The α-APM content converted to free amine was 21.4 g. The ratio of α-APM:β-APM was 99.5:0.5.

The recovery ratio based on original α-APM was 91.1%.

EXAMPLE 8

To 133.2 g of an acetic acid solution containing 14.7 g (0.05 mole) of α-APM and 14.7 g (0.05 mole) β-APM, 5.2 g (0.052 mole) of 98% sulfuric acid was added over 30 minutes at 20°–25° C. The mixture was stirred for an hour at the same temperature. Thereafter the precipitated crystals were filtered, washed and dried. The isolated crystals of the sulfuric acid salt of α-APM weighed 17.2 g. The crystals thus obtained were analyzed by high performance liquid chromatography. The α-APM content converted to free amine was 12.8 g. The ratio of α-APM:β-APM was 99.1:0.9.

The recovery based on original α-APM was 87.0%.

EXAMPLE 9

The same procedures as described in Example 2 were carried out except that propionic acid was used as the organic carboxylic acid. The yield was 30.3 g.

The crystals thus obtained was analyzed by high performance liquid chromatography. The α-APM content converted to free amine was 22.5 g.

The recovery based on original α-APM was 95.7%. The crystals were identified as the sulfuric acid salt of α-APM by elementary analysis.

EXAMPLE 10

The same procedures as described in Example 5 were carried out except that 133.2 g of toluene was further added. The yield was 28.5 g.

The crystals thus obtained were analyzed by high performance liquid chromatography. The α-APM content converted to free amine was 21.2 g.

The recovery based on original α-APM was 90.2%.

EXAMPLES 11–15

The same procedures as described in Example 2 were carried out except that the organic carboxylic acids and mineral acids as illustrated in Table 1 were used.

The results are shown in Table 1.

TABLE 1

| Example | Organic carboxylic acid | Mineral acid Type | Amount (g) | α-APM Mineral acid salt Yield (g) | Recovery (%) |
|---|---|---|---|---|---|
| 11 | Formic acid | 98% Sulfuric acid | 10.5 | 27.6 | 88.0 |
| 12 | Acetic acid | Hydrogen chloride gas | 3.8 | 18.5 | 70.0 |
| 13 | Propionic acid | 98% Nitric acid | 10.5 | 26.9 | 94.2 |
| 14 | Propionic acid | 85% Phosphoric acid | 12.1 | 28.2 | 89.9 |
| 15 | Acetic acid | 70% Sulfuric acid | 14.7 | 29.5 | 94.0 |

COMPARATIVE EXAMPLE 1

To 500 ml of an aqueous solution containing 5.0 g (0.017 mole) of α-APM and 5.0 g (0.017 mole) of β-APM, 6.0 g (0.039 mole) of β-resorcylic acid was added and stirred for 5 hours at the room temperature. The mixture was held overnight in a refrigerator. The crystals which precipitated were filtered and dried. The crystals obtained weighed 9.3 g. The crystals were treated with base in the usual method to give 4.0 g of free α-APM.

The recovery based on original α-APM was 80%.

COMPARATIVE EXAMPLE 2

In 50 ml of 1N hydrochloric acid, 5.0 g (0.017 mole) of α-APM and 5.0 g (0.017 mole) of β-APM were dissolved at room temperature. Crystals were immediately deposited. The mixture was held overnight in a refrigerator. The precipitated crystals were filtered to obtain 4.8 g of hydrochloric acid salt of α-APM.

The crystals thus obtained were converted to free α-APM, which was analysed and found to be of high purity.

The recovery based on original α-APM was 72%.

EXAMPLE 16

To 133.2 g of an acetic acid solution containing 22.1 g (0.075 mole) of α-APM and 7.4 g (0.025 mole) of β-APM, 10.6 g (0.105 mole) of 98% methanesulfonic acid as added over 30 minutes at 20°-25° C. The mixture was stirred for an hour at the same temperature. Thereafter he precipitated crystals were filtered, washed and dried. The isolated crystals of the methanesulfonic acid salt weighed 26.7 g. The crystals thus obtained were analyzed by high performance liquid chromatography. The α-APM content converted to free amine was 26.4 g. The ratio of α-APM:β-APM was 99.0:1.0.

The recovery based on original α-APM was 90.0%.

Results of elementary analysis coincided with the methanesulfonic salt of α-APM.

| | Elementary analysis (%) $C_{15}H_{22}N_2O_6S$ | | | |
|---|---|---|---|---|
| | C | H | N | S |
| Found | 46.01 | 5.73 | 7.16 | 8.05 |
| Calculated | 46.15 | 5.68 | 7.18 | 8.21 |

EXAMPLE 17

To 133.2 g of an acetic acid solution containing 23.5 g (0.08 mole) of α-APM and 5.9 g (0.02 mole) of β-APM, 10.6 g (0.105 mole) of 98% methanesulfonic acid was added over 30 minutes at 20°-25° C. The mixture was stirred for an hour at the same temperature. Thereafter the precipitated crystals were filtered, washed and dried. The isolated crystals of the methanesulfonic acid salt of α-APM weighed 29.8 g. The crystals thus obtained were analyzed by high performance liquid chromatography. The α-APM content converted to free amine was 22.3 g. The ratio of α-APM:β-APM, was 99.0:1.0.

The recovery based on original α-APM was 95.0%.

To 178 g of water, 20 g of the crystals was added. The solution thus obtained was neutralized to pH 5.6 by the addition of sodium hydrogen carbonate and cooled to 5° C. Precipitated crystals were filtered, washed with cold water and dried. The yield of crystals of α-APM was 18.7 g.

Angle of rotation: $[\alpha]_D^{20} + 15.6$ ($C=4.15N$ formic acid)

According to analysis by high performance liquid chromatography, the crystals thus obtained were high purity α-APM.

EXAMPLE 18

To 133.2 g of an acetic acid solution containing 23.5 g (0.08 mule) of α-APM, 5.2 g (0.02 mole) of β-APM, and 2.5 g (0.0089 mole) of α-L-aspartyl-L-phenylalanine, 11.0 g (0.114 mole) of methanesulfonic acid was added over 30 minutes at 20°-25° C. The mixture was stirred for an hour at the same temperature. Thereafter the precipitated crystals were filtered, washed and dried.

The yield of isolated crystals of the methanesulfonic acid salt of α-APM was 27.8 g.

The crystals thus obtained were analyzed by high performance chromatography. The α-APM content converted to free amine was 20.9 g. Results of elementary analysis were coincided with methanesulfonic acid salt of α-APM.

The recovery based on original α-APM was 89.0%.

EXAMPLE 19

To 235 g of an acetic acid solution containing 23.5 g (0.08 mole) of α-APM, 5.9 g (0.02 mole) of β-APM, 2.5 g (0.0089 mole) of α-L-aspartyl-L-phenylalanine, and 0.6 g (0.0021 mole) of β-L-aspartyl-L-phenylalanine, 11.2 g (0.117 mole) of methanesulfonic acid was added over 30 minutes at 20°-25° C. The mixture was stirred for an hour at the same temperature. Thereafter the precipitated crystals were filtered, washed and dried. The isolated crystals of the methanesulfonic acid salt of α-APM weighed 27.6 g.

The crystals thus obtained were analyzed by high performance liquid chromatography. The α-APM content converted to free amine was 20.8 g. The ratio of α-APM:β-APM was 99.5:0.5. The recovery based on original α-APM was 88.0%.

EXAMPLE 20

To 235 g of an acetic acid solution containing 23.5 g (0.08 mole) of α-APM, 5.9 g (0.02 mole) of β-APM, 2.5 g (0.0089 mole) of α-L-aspartyl-L-phenylalanine, 0.6 g (0.0021 mole) of β-L-aspartyl-L-phenylalanine, and 0.6 g (0.0023 mole) of 5-benzyl-3,6-dioxopiperazine-2-acetic acid, 11.2 g (0.117 mole) of methanesulfonic acid was added over 30 minutes at 20°–25° C. The mixture was stirred for an hour at the same temperature. Thereafter the precipitated crystals were filtered, washed and dried. The yield of isolated crystals of the methanesulfonic acid salt of α-APM were 27.7 g. The crystals thus obtained were analyzed by high performance liquid chromatography. The α-APM content converted to free amine was 20.8 g. The ratio of α-APM:β-APM was 99.5:0.5.

The recovery based on original α-APM was 88.3%.

EXAMPLE 21

The same procedures as described in Example 17 were carried out except that propionic acid was used in place of acetic acid. The yield was 28.1 g.

The crystals thus obtained were analyzed by high performance liquid chromatography. The α-APM content converted to free amine was, 21.2 g.

The recovery based on original α-APM was 90.2%.

EXAMPLE 22

The same procedures as described in Example 18 were carried out except that 133.2 g of toluene was further added. The yield was 27.6 g.

The crystals thus obtained were analyzed by high performance liquid chromatography. The α-APM content converted to free amine was 20.8 g. The recovery based on original α-APM was 88.7%.

EXAMPLES 23–26

The same procedures as described in Example 17 were carried out except that organic carboxylic acids and organic sulfonic acids were used as shown in Table 2. The results are illustrated in Table 2.

The results of elementary analysis coincided with the sulfuric acid salt of α-APM.

| Elementary analysis (%) $C_{14}H_{20}N_2O_9S$ | | | | |
|---|---|---|---|---|
| | C | H | N | S |
| Found | 42.76 | 5.33 | 7.12 | 8.16 |
| Calculated | 42.86 | 5.14 | 7.14 | 8.17 |

To 180 g of water, 20 g of the thus-obtained crystals was added. The solution thus obtained was neutralized to pH 5.2 by the addition of sodium hydrogen carbonate and cooled to 5° C. Precipitated crystals were filtered, washed with cold water and dried. Crystals of α-APM weighing 14.2 g were obtained.

Angle of rotation: $[\alpha]_D^{20} = 15.8$ ($C = 4.15N$ formic acid)

According to analysis by high performance liquid chromatography, the crystals thus obtained were high purity α-APM.

EXAMPLE 28

To 428 g of an acetic acid solution containing 34.3 g (0.08 mole) of Z-α-APM and 8.6 g (0.02 mole) of Z-β-APM, 2.1 g of 5% palladium carbon was added and catalytic reduction was carried out at atmospheric pressure for 2 hours at room temperature. After finishing the reaction, the catalyst was filtered, and 10.6 g (0.105 mole) of 98% methanesulfonic acid was added to the filtrate over 30 minutes. The mixture was stirred for an hour at the same temperature. Thereafter the precipitated crystals were filtered, washed and dried. The isolated crystals of the methanesulfonic acid salt of α-APM weighed 28.1 g.

The crystals thus obtained were analyzed by high

TABLE 2

| | | | | α-APM | |
|---|---|---|---|---|---|
| | Organic | Organic sulfonic acid | | Organic sulfonic acid | |
| Example | carboxylic acid | Type | Amount (g) | salt Yield (g) | Recovery (%) |
| 23 | Formic acid | Methanesulfonic acid | 10.5 | 27.5 | 88.0 |
| 24 | Acetic acid | Trifluoromethane-sulfonic acid | 15.8 | 32.2 | 90.6 |
| 25 | Propionic acid | Trifluoromethane-sulfonic acid | 15.8 | 32.1 | 90.2 |
| 26 | Propionic acid | Trifluoromethane-sulfonic acid | 15.8 | 32.0 | 90.0 |

EXAMPLE 27

To 428 g of an acetic acid solution containing 34.3 g (0.08 mole) of Z-α-APM and 8.6 g (0.02 mole) of Z-β-APM, 2.1 g of 5% palladium carbon was added and catalytic reduction was carried out at atmospheric pressure for 2 hours at room temperature. After finishing the reaction, the catalyst was filtered, and 10.5 g (0.105 mole) of 98% sulfuric acid was added to the filtrate over 30 minutes. The mixture was stirred for an hour at the same temperature. Thereafter the precipitated crystals were filtered, washed and dried. The yield of isolated crystals was 29.8 g.

The crystals thus obtained were analyzed by high performance liquid chromatography. The α-APM content converted to free amine was 22.1 g. The ratio of α-APM:β-APM was 99.0:1.0. The recovery based on original α-APM was 94%.

performance liquid chromatography. The α-APM content converted to free amine was 17.5 g. The ratio of α-APM : β-APM was 99.0 : 1.0. The recovery based on original α-APM was 88%.

The results of elementary analysis were coincided with methanesulfonic acid salt of α-APM.

| Elementary analysis (%) $C_{15}H_{22}N_2O_8S$ | | | | |
|---|---|---|---|---|
| | C | H | N | S |
| Found | 46.06 | 5.71 | 7.17 | 8.09 |
| Calculated | 46.15 | 5.68 | 7.18 | 8.21 |

EXAMPLE 29

Catalytic reduction was carried out with the same procedures as described in Example 27 by using a mixture of Z-α-APM and Z-β-APM having the same composition as Example 27, except that 2.1 g of platinum carbon was used as the catalyst. To the reaction mixture obtained by the catalytic reduction, after removal of the catalyst 11.0 g (0.105 mole) of 35% hydrochloric acid was added over 30 minutes and stirred for an hour at the same temperature. The precipitated crystals were filtered, washed and dried. The crystals obtained weighed 23.8 g.

The crystals thus obtained were analyzed by high performance liquid chromatography. The α-APM content The ratio of α-APM:β-APM was 99.5:0.5.

The recovery based on original α-APM was 90%.

Results of elementary analysis coincided with the hydrochloric acid salt of α-APM.

| Elementary analysis (%) $C_{14}H_{19}ClN_2O_5$ | | | | |
|---|---|---|---|---|
| | C | H | N | Cl |
| Found | 50.70 | 5.83 | 8.35 | 10.53 |
| Calculated | 50.84 | 5.79 | 8.47 | 10.72 |

To 180 g of water, 20 g of the crystals were added. The solution thus obtained was neutralized to pH 5.2 by the addition of 28% aqueous ammonia and cooled to 5° C. Precipitated crystals were filtered, washed with cold water and dried. Crystals of α-APM weighing 14.0 g were obtained.

According to the analysis by high performance liquid chromatography, the crystals thus obtained were high purity α-APM.

EXAMPLE 30

Catalytic reduction was carried out by using the same procedures as described in Example 27 except that propionic acid was used as the solvent in place of acetic acid. α-APM was isolated in the form of its sulfuric acid salt. The yield was 29.9 g.

The product was analyzed by high performance liquid chromatography. The α-APM content converted to free amine was 22.1 g.

The recovery based on original α-APM was 94%. The ratio of α-APM:β-APM was 98.8:1.2.

EXAMPLE 31

Sulfuric acid salt of α-APM was isolated by using the same procedures as described in Example 27 except that acetic acid containing 20% toluene by weight was used as solvent. The yield was 30.4 g.

The thus-produced sulfuric acid salt of α-APM was analyzed by high performance liquid chromatography. The α-APM content converted to free amine was 22.1 g. The recovery based on original α-APM was 94%. The ratio of α-APM:β-APM was 98.5:1.5.

EXAMPLE 32

The same procedures as described in Example 27 were carried out using 428 g of an acetic acid solution containing 32.1 g (0.075 mole) of Z-α-APM, 8.6 g (0.02 mole) of Z-β-APM, 2.1 g (0.005 mole) of N-benzyloxycarbonyl-α-L-aspartyl-L-phenylalanine and 0.1 g (0.00038 mole) of 5-benzyl-3,6-dioxopiperazine-2-acetic acid. After the catalytic reduction was completed and the catalyst removed, the thus-produced sulfuric acid salt of α-APM was isolated by the same procedures as described in Example 27. The yield was 27.7 g.

The sulfuric acid salt was analyzed by high performance liquid chromatography. The α-APM content converted to free amine was 20.5 g. The recovery based on original α-APM was 93%. The ratio of α-APM:β-APM was 99.0:1.0. α-L-Aspartyl-L-phenylalanine and 5-benzyl-3,6-dioxopiperazine were not detected.

EXAMPLES 33–36

The same procedures as described in Example 27 were carried out by using various organic carboxylic acid solvents and mineral acids as illustrated in Table 3. The results are shown in Table 3. In each instance, high purity α-APM was obtained.

TABLE 3

| | Organic | Mineral acid | | α-APM | |
|---|---|---|---|---|---|
| Example | carboxylic acid | Type | Amount (g) | Mineral acid salt Yield (g) | Recovery (%) |
| 32 | Formic acid | 98% Sulfuric acid | 10.5 | 28.9 | 92.2 |
| 33 | Acetic acid | Hydrogen chloride gas | 3.8 | 25.5 | 96.5 |
| 34 | Propionic acid | 98% Nitric acid | 10.5 | 26.7 | 93.6 |
| 35 | Propionic acid | 85% Phosphoric acid | 12.1 | 28.6 | 91.0 |

What is claimed is:

1. A method for the separation of α-L-aspartyl-L-phenylalanine methyl ester (α-APM) from a solution thereof in an organic solvent comprising an organic carboxylic acid, which comprises the steps of precipitating the α-APM from the solution by converting the α-APM with sulfuric acid or an organic sulfonic acid to an acid addition salt thereof, and separating the precipitated α-APM acid addition salt from the solvent.

2. The method of the claim 1, wherein both the solvent and organic carboxylic acid are acetic acid.

3. The method of claim 1, wherein α-APM is converted to a salt thereof with sulfuric acid.

4. The method of claim 1, wherein the sulfuric acid is 98% sulfuric acid.

5. The method of claim 1, wherein said solution consists essentially of said α-APM and said organic carboxylic acid.

6. The method of claim 1, wherein the organic solvent is a hydrocarbon, a carboxylic acid ester, or an ether.

7. The method of claim 1 comprising the further step of converting the separated salt of α-APM with base to α-APM.

8. A method for the purification of crude α-L-aspartyl-L-phenylalanine methyl ester (α-APM) which comprises converting the crude α-APM into an acid addition salt thereof with sulfuric acid or an organic sulfonic acid while in admixture with an organic solvent solution comprising an organic carboxylic acid and separating the thus-produced highly pure sulfuric acid or organic sulfonic acid salt of α-APM.

9. The method of claim 8, wherein the crude α-APM is a reaction product obtained by hydrogenating N-benzyloxycarbonyl-α-L-phenylalanine methyl ester (Z-APM) in the presence of a hydrogenation catalyst as a solution in the organic carboxylic acid or in an organic solvent solution containing the organic carboxylic acid.

10. The method of claim 8, wherein the sulfuric acid is 98% sulfuric acid.

11. The method of claim 8, wherein both the solvent and the organic acid are acetic acid.

12. The method of claim 8, wherein the crude α-APM is converted to a salt thereof with sulfuric acid.

13. The method of claim 8, wherein the crude α-APM consists essentially of 60-APM and β-APM.

14. The method of claim 13, wherein both the solvent and the organic carboxylic acid are acetic acid and wherein the crude α-APM is converted to a salt thereof with sulfuric acid.

15. The method of claim 14, wherein the crude α-APM is a reaction product obtained by hydrogenating N-benzyloxycarbonyl-α-L-aspartyl-L-phenylalanine methyl ester (Z-APM) in the presence of a hydrogenation catalyst as a solution in the organic carboxylic acid or in an organic solvent solution containing the organic carboxylic acid.

16. The method of claim 14, wherein the sulfuric acid is 98% sulfuric acid.

17. The method of claim 8 comprising the further step of converting the separate salt of α-APM with base to a α-APM.

18. The method of claim 17, wherein the crude α-APM is a reaction product obtained by hydrogenating N-benzyloxycarbonyl-α-L-aspartyl-L-phenylalanine methyl ester (Z-APM) in the presence of a hydrogenation catalyst as a solution in the organic carboxylic acid or in an organic solvent solution containing the organic carboxylic acid.

19. In a process for the production of α-L-aspartyl-L-phenylalanine methyl ester (α-APM) by the catalyzed hydrogenation of N-benzyloxycarbonyl-α-L-aspartyl-L-phenylalanine methyl ester (Z-APM) as a solution thereof in acetic acid, the improvement which comprises isolating pure α-APM from the reaction mixture, after removal of the hydrogenation catalyst, as an acid addition salt thereof by the addition of sulfuric acid or an organic sulfonic acid thereto, separating the pure salt of α-APM which precipitates therefrom; and converting the separated acid addition salt of α-APM with base to α-APM.

20. The process of claim 19, wherein the acid added to the reaction mixture is sulfuric acid.

21. The method of claim 20, wherein the sulfuric acid is 98% sulfuric acid.

22. The process of claim 19, wherein the separated salt of α-APM is dissolved in water and the α-APM produced with the base is crystallized therefrom.

23. A method for the separation of α-L-aspartyl-L-phenylalanine methyl ester (α-APM) from a solution thereof in an organic solvent consisting solely of an organic carboxylic acid, which comprises the steps of precipitating the α-APM from the solution by converting the α-APM with phosphoric acid to an acid addition salt thereof, and separating the precipitated α-APM acid addition salt from the solvent.

24. A method for the purification of crude α-L-aspartyl-L-phenylalanine methyl ester (α-APM) which comprises converting the crude α-APM into an acid addition salt thereof with phosphoric acid while in admixture with an organic solvent consisting solely of an organic carboxylic acid and separating the thus-produced highly pure phosphoric acid salt of α-APM.

* * * * *